United States Patent [19]

Niznick

[11] Patent Number: 5,571,017
[45] Date of Patent: Nov. 5, 1996

[54] SELECTIVE SURFACE, EXTERNALLY-THREADED ENDOSSEOUS DENTAL IMPLANT

[75] Inventor: Gerald A. Niznick, Las Vegas, Nev.

[73] Assignee: Core-Vent Corporation, Las Vegas, Nev.

[21] Appl. No.: 318,231

[22] Filed: Oct. 5, 1994

[51] Int. Cl.$^6$ .................................................. A61C 8/00
[52] U.S. Cl. ............................................ 433/174; 433/173
[58] Field of Search .................................. 433/172, 173, 433/174, 175, 176

[56] References Cited

U.S. PATENT DOCUMENTS

| | | | |
|---|---|---|---|
| 5,078,607 | 1/1992 | Niznick | 433/174 |
| 5,174,755 | 12/1992 | Fukuda | 433/173 |
| 5,324,199 | 6/1994 | Branemark | 433/174 |
| 5,338,197 | 8/1994 | Kwan | 433/174 |
| 5,417,569 | 5/1995 | Perisse | 433/173 |

*Primary Examiner*—Christopher A. Bennett

[57] ABSTRACT

Endosseous dental implants having generally cylindrical-shaped bodies and self-tapping threads at the distal end and, in some case, external threads over a substantial portion of their external surface, include internal or external wrench-engaging surfaces at the proximal end portion and, between the relatively smooth distal and proximal end portions, an external middle region having greater surface roughness than the proximal or distal ends, or a coating, to promote attachment of the implant to bone tissue when the implant is placed in a generally-cylindrical passage formed in bone tissue to receive the implant.

24 Claims, 2 Drawing Sheets

000
SELECTIVE SURFACE, EXTERNALLY-THREADED ENDOSSEOUS DENTAL IMPLANT

BACKGROUND OF THE INVENTION

Current State of the Art of Externally-Thread Implants

Implants with threads over a substantial portion of their external surface, designed for self-tapping insertion, are generally known and commercially available. These screw implants usually have an unthreaded, annular portion at the proximal end of the implant that is commonly referred to as the neck portion, with the remainder of the external surface substantially threaded to or near to the distal end of the implant. The self-tapping features located in the threaded surface near the distal end of the implant are the subject of several patents (Linkow U.S. Pat. No. 4,713,004; Jorneus U. S. Pat. No. 5,269,685). These features serve the function of cutting the threads in the cylindrical passage formed in the jawbone tissue of a person to receive the implant as the externally-threaded implant is rotated to a depth that places the neck of the implant above, at or just below the crest of the jawbone.

Self-tapping insertion of an externally-threaded implant is accomplished by forming, as by machining, one or more grooves on the sidewall extending upwardly from the distal end parallel to the longitudinal axis of the dental implant and through at least one full diameter external thread. These grooves create cutting edges that function to scrape off bone chips during threading of the implant into the cylindrical hole prepared in the bone tissue. The grooves also provide cavities with adequate volume to contain the bone tissue material to allow full seating of the implant.

Some self-tapping implants also provide a through-hole connecting two channels on opposite sides of the implant to provide additional cavity space to harbor bone chips and to further stabilize the implant once bone regeneration has occurred. Self-tapping insertion of the implant has proven advantageous from a time-saving standpoint (Fribert B. et al.; JOMI 1992; 1:80–84) by reducing surgical time by 3 minutes or more per implant. Self-tapping insertion of the externally-threaded implants also improves the initial stability needed for direct bone attachment following a healing period, referred to as osseointegration, by creating a more intimate contact with the bone than placement following use of a bone tap surgical instrument. This more intimate initial fit has also been demonstrated to result in an increased percentage of bone attachment to the implant surface after healing (Cook S. et al. J Oral Implant 1993: 4:288–294). For self-tapping insertion to be effective in dense bone, the cutting edges created by the grooves through the distal threads must be sharp enough to shave bone chips. Roughening the implant surface by grit-blasting, or by grit-blasting followed by coating the surface of the implant with a spray of molten titanium called Titanium Plasma Spray (TPS) or coating the surface with a bio-reactive material such as Hydroxylapatite (HA), rounds these cutting edges, decreasing the cutting efficiency of the self-tapping features. This can necessitate increasing the torque forces needed to insert the self-tapping implant in dense bone to the point that damage may occur to the wrench-engaging feature in the proximal portion of the implant, resulting in failure to seat the implant fully in the bone chamber.

Self-tapping screw implants are usually machined from a biocompatible metal of suitable strength such as commercially-pure titanium or from medical grade titanium alloy. The selection of Grade 1 or 2 commercially-pure (CP) titanium, with tensile strengths lower than Grade 3 or 4 CP titanium or titanium alloy (6Al/4V), may preclude the incorporation of through-holes because of the lower tensile strength. Such lower tensile strength may also limit the density of bone that the implant can self-tap into because of the lower resistance to distortion of the wrench-engaging surfaces at or near the proximal end of the implant as higher torque forces are required to cut through dense bone.

Some self-tapping screw implants are sold with a machined surface (Nobelpharma and Implant Innovations, Inc. implants) and others (Core-Vent Corporation's SCREW-VENT, SWEDE-VENT and CORE-VENT implants) are further treated after machining by washing in dilute HF acid to remove loose titanium particles and other contaminants. Acid etching creates pits on the surface of the implant, increasing the surface roughness, compared to the untreated machined surface, as measured by the average distance between the peaks and valleys created on the surface in the form of machining grooves or etch pits. Some commercially available self-tapping screw implants have their threaded external surfaces treated to increase surface roughness while maintaining the neck portion relatively smooth by leaving it with a machined or etched surface or by mechanically polishing the surface. The texture of the implant's external surface is increased in roughness by grit-blasting with a variety of bio-compatible particles such as titanium oxide (Astra implants) or aluminum oxide (CORE-VENT implant, pre-1986). The degree of roughness can be varied by varying the size of the abrasive particles and by varying the force and the duration of the blasting procedure. Some screw implants, after machining, are grit-blasted to roughen the surface preparatory to applying a coating of either Titanium Plasma Spray (TPS: Straumann's implant), which provides both a rough and porous surface, or a coating of a bio-active material such as Hydroxylapatite (HA: STERI-OSS, SCREW-VENT and SWEDE-VENT implants). HA may be densely applied and of high crystallinity, which produces a surface roughness approximating that of acid etching or less dense and/or less crystalline which produces a surface roughness that could match or exceed that of TPS coating or grit-blasting.

Surface Texture and Material Effect Bone Attachment

Studies have documented increased removal torques with implants having increased surface roughness (Carlsson, Albrektsson et al., JOMI 1988: Vol. 3), and other studies have shown increased bone attachment to rougher surfaces (Buser: J Biomet Mater Re 1991: Vol. 25). A study comparing bone attachment to HA coated and machined surfaces demonstrated a faster, more complete attachment to the HA surface in the critical, early healing period (Gottlander M., Albrektsson T.: JOMI 1991: Vol. 4).

At the cellular level, one study found higher levels of attachment of osteoblast-like cells to surfaces with random roughness created by grit-blasting and acid etching compared to parallel grooved surfaces similar in appearance to a machined surface, created in this study by grinding the surface with 120 and 60 gauge grit. This was true despite the fact that the surface roughness of the grooved surface, created by grit polishing, was rougher than that produced by the acid etch procedure, indicating that random roughness promotes bone attachment better than parallel or concentric grooves.

Another study comparing bone attachment strength to HA and to a rougher grit-blasted surface documented 77% increase in torsional strength for the HA coated surface, indicating that HA is bio-active and created a chemical as well as mechanical bond with the bone.

Studies have measured the differences in surface roughness of commercially-available implants using scanning microscope profilometry (Albrektsson JOMI 6:1993), and determined that the machined Branemark surface was the smoothest with an average difference of about 10 microns between the peaks and valleys of the surface texture. Using the same measurement standard, the acid etched surface of a SCREW-VENT, made from commercially-pure titanium, measured an average of about 10 microns; the acid-etched surface of the titanium alloy Core-Vent measured an average of about 18 microns. The difference may be due to the response of the different metals to acid etching, but is more likely due to the etch time the implants were subjected to. The TPS coated surface of the IMZ implant measured an average peak-to-valley difference of about 25 microns. HA coated surfaces of four implants were measured in this study with the average difference from peak-to-valley measuring about 18 microns for Calcitek's highly dense, crystalline HA surface. Several other HA coatings, which are more porous and less crystalline, were measured with surface roughnesses ranging up to 40 microns.

Regardless of the smoothness of the HA surface, it is unsuitable material for coating the neck portion of an implant that may become exposed to oral mucosa when crestal bone recession occurs around the top of the implant. Coated surfaces so exposed to the oral environment either increase the attachment of dental plaque, or dissolve, exposing the rough, grit-blasted undersurface, which also increases the attachment of dental plaque. Plaque around the exposed neck of an implant causes adverse mucosal tissue reactions and ultimately increased bone loss, just as with natural teeth. Crestal bone cratering and associated soft tissue complications have been reported with Calcitek's non-threaded cylinder implants that have a dense, relatively smooth, HA coating all the way to the top of the implant (Johnson; Calif. Dental Journal, JOMI 1994, Special Supplement). Non-threaded cylinder implants have been shown, in photoelastic studies (French A.: Inter J. of Perio Rest Dent 1989 3:220–230), to be less able to distribute vertical and lateral forces or to resist compressive and shear forces than threaded implants because of their reduced surface area. This design factor most likely contributed to the complications reported with HA coated cylinder implants in the Johnson study.

Exposure of the machined surface of the neck of the implant above the crest of the bone routinely occurs with the Branemark implants because of the countersinking surgical step required to seat the wider neck of that implant, but long-term studies do not indicate that such exposure of the machined surface to mucosal tissue attracts dental plaque any more than with natural teeth. Oral hygiene can be maintained on this relatively smooth surface, minimizing soft tissue complications.

The clinical complications of exposure of the rough TPS coating into the gingival crevice have been documented in a clinical study of 54 ITI implants where all the implants osseointegrated. However, within 3 years, 3 implants exhibited recurrent per-implant infections and were classified as late failures (Buser JOMI 1991, Vol. 4).

Implant manufacturers, recognizing the potential benefits of the bio-active HA coatings and the rougher surfaces of the TPS coatings, have attempted to limit the complications associated with exposure to these rough or bio-reactive surfaces to the oral cavity by maintaining an uncoated metal portion extending down from the top of the TPS or HA coated implant a distance ranging from 0.5 mm to over 2 mm in length.

SUMMARY OF THE INVENTION

This invention relates to externally-threaded, endosseous dental implants. More particularly, this invention relates to externally-threaded endosseous dental implants with generally cylindrical-shaped bodies, with self-tapping threads at or near the distal end of the implant, with internal or external wrench-engaging surfaces at or near the proximal end of the implant, and with an internal passage extending into the body of the implant from an opening at the proximal end of the implant that receives and engages a separate, secondary part, sometimes called an abutment or an adaptor.

The endosseous dental implants of this invention have generally cylindrical-shaped bodies or bodies that taper slightly to a smaller diameter towards the distal end and are externally-threaded over a substantial portion of their external surface. In preferred embodiments, the distal end also includes a longitudinal groove on the sidewall extending through the external threads and extending upwardly from the distal end of the dental implant parallel to the longitudinal axis of the dental implant itself. In some embodiments, these implants also include one or more through-holes near the distal end perpendicular to the longitudinal axis of the dental implant. In some of these embodiments, the through-hole communicates with the distal end of the implant via a vertical through-hole extending into the body of the implant from the distal end of the implant to the through-hole.

In preferred embodiments, three specific areas of the external surface of the screw implant can be distinguished by both design features and surface roughness or surface coating material to improve clinical success. The neck is preferably unthreaded, uncoated and relatively smooth to allow maintenance of oral hygiene should the neck become exposed to the oral environment. The threaded distal end of the implant is preferably uncoated and has a smooth enough surface to maintain sharp cutting threads for self-tapping insertion, thereby shortening surgical time and improving initial stability. The middle, preferably threaded, portion of the implant is roughened, or coated with a bio-active material such as HA, or both, to increase the percentage of the surface in contact with bone, thus enabling the implant to better withstand biting forces. These self-tapping screw implants provide long-term implant stability in bone, reduce surgical time for implantation, and minimize clinical complications.

In preferred embodiments, the proximal end of these dental implants has an uncoated, annular portion, referred to as the neck portion, that has a smooth, machined surface. The neck portion, in some embodiments, is acid etched to remove loose titanium particles from the surface and to create a slightly rougher pitted surface. Acid etched surfaces have been shown in studies to provide an acceptable surface for attachment of both mucosal and bone tissue (Schupback P. et al.: Clin Oral Impl. res. 1994 5:55–65). In preferred embodiments, the neck portion of the implant is sufficiently smooth to minimize adherence of dental plaque that can cause an adverse mucosal tissue reaction if exposed to the oral environment as a result of crestal bone loss or otherwise. An average surface roughness of approximately 10 microns is preferred, but up to 20 microns is acceptable, as measured by the average difference between the peaks and valleys of the surface texturing using appropriate measuring devices such as Scanning Microscope Profilometers.

In preferred embodiments, the middle portion of the external surface of the implant, whether threaded or unthreaded, has surface roughness sufficient to promote improved bone attachment. Preferably, this surface is coated with a bio-reactive material such as HA. In general, this surface is at least about 25% rougher than the external surface of the relatively smooth, annular neck portion of the implant, or the external surface of the threaded distal portion of the implant.

The threaded distal portion of the annular neck portion and the implant preferably have a surface roughness, measured by the average peak-to-valley distance of the surface texture, of up to 20 microns. In contrast, the surface of the threaded middle portion of the implant, if uncoated, has a surface roughness measured by the average peak-to-valley distance of the surface texture of 25 microns or greater. The increased roughness of this middle portion of the external surface of the implant may be formed by HA coating, TPS coating or grit-blasting of the implant surface. Coating this threaded, middle portion with a bio-reactive. material such as HA provides improved bone attachment, regardless of its surface roughness.

In preferred embodiments, the roughness of the surface of the relatively rough, threaded middle portion of the implant is attributable to Hydroxylapatite (HA) coating, TPS (Titanium Plasma Spray) coating, grit blasting, or other bombardment with particulates of sufficient size and for a sufficient time at a sufficient pressure to create the desired roughness over at least 90% of the area of this portion.

In some preferred embodiments, the HA coating on the threaded middle portion of the implant has a high crystallinity which reduces solubility but maintains bio-active benefits that encourage stronger, more rapid bone attachment. Such high crystalline HA may have a surface roughness approximating 20 microns, the upper limits of the relatively smooth neck and distal threaded portion. However, before the HA coating can be firmly attached to the implant surface, the surface must be roughened to at least 25 microns as measured by the average peak-to-valley distance of the surface texture, as, for example, by grit blasting.

In preferred embodiments, the distal threaded portion of the dental implant is uncoated, and the middle threaded portion is at least 25% rougher than the distal portion, if the middle threaded portion is uncoated. In preferred embodiments, longitudinal grooves are cut through the threads on the distal portion of the implant to enhance self-tapping insertion.

In some embodiments, the surface of this distal portion is machined. In preferred embodiments, however, the distal portion has an acid-etched surface. Such a surface results from acid etching with a concentration of HF or other suitable acid capable of controlled removal of approximately 0.001 inch of the surface when used in the appropriate concentration and for the appropriate time to create the desired surface texture measuring, on average, less than 20 microns difference between peak-to-valley. Acid etching not only increases surface roughness to promote increased bone attachment (Carlsson, Albrektsson et al.: JOMI 1988, Vol. 3 and Buser: J Biomet Mater Re 1991: Vol. 25), but also removes loose titanium particles formed on the implant surface during the machining process. One study showed that these particles become embedded in the walls of the cylindrical bone socket during self-tapping insertion of the threaded implant (Schliephake 1993, JOMI Vol. 8).

In preferred embodiments, one or more longitudinal grooves on the sidewalls extend through the external threads in the distal portion, upwardly from or near the distal end of the dental implant parallel to the longitudinal axis of the dental implant itself, creating relatively sharp edges and relief areas for cutting and harvesting bone chips during self-tapping insertion in dense bone. In some embodiments, the distal portion also includes one or more through-holes. Some of these embodiments also include a cavity inside the implant near the distal end as additional space for bone chips and to increase stabilization of the implant after healing and bone regeneration has occurred.

The proximal end of these dental implants preferably includes either internal, wrench-engaging surfaces or external, wrench-engaging surfaces. Preferably, these wrench-engaging surfaces are multi-sided and more preferably have six or eight sides and, if external, are formed on the surface at the top of the implant, as in Core-Vent Corporation's SWEDE-VENT® implant. If internal, the multi-sided surfaces lie just below the upper surface of the implant inside an internal passage, as in Core-Vent Corporation's SCREW-VENT® implant.

In preferred embodiments, whether the implants have external or internal wrench-engaging surfaces, the implants also include an internal passage for receiving and engaging a secondary implant part, sometimes called a post, adapter or abutment. Where the internal passage is threaded, at least in part, the abutment can be externally threaded to engage the internal threads inside this passage, or the abutment can be cementable inside this internal passage. Suitable abutments may be one-piece, two-piece or three-piece and, if multi-part, may include a portion that interfits with internal or external wrench-engaging surfaces to minimize rotation of the abutment in relation to the implant itself, as in Core-Vent Corporation's SWEDE-VENT® TL dental implants.

BRIEF DESCRIPTION OF THE DRAWINGS

The roughened implants of this invention can better be understood by reference to the drawings, in which:

Both the implants of FIG. 1 and of FIG. 2 have an internally threaded passage to engage externally-threaded abutments. FIG. 1 shows an external, wrench-engaging, multi-sided surface for engaging a tool to place the implant into a generally cylindrical passage formed in a person's jawbone to receive the implant. The implant of FIG. 2 has a wrench-engaging, multi-sided surface just below the top surface of the implant, and within the internal passage inside the implant.

DETAILED DESCRIPTION OF THE PREFERRED EMBODIMENTS

Figure 1:
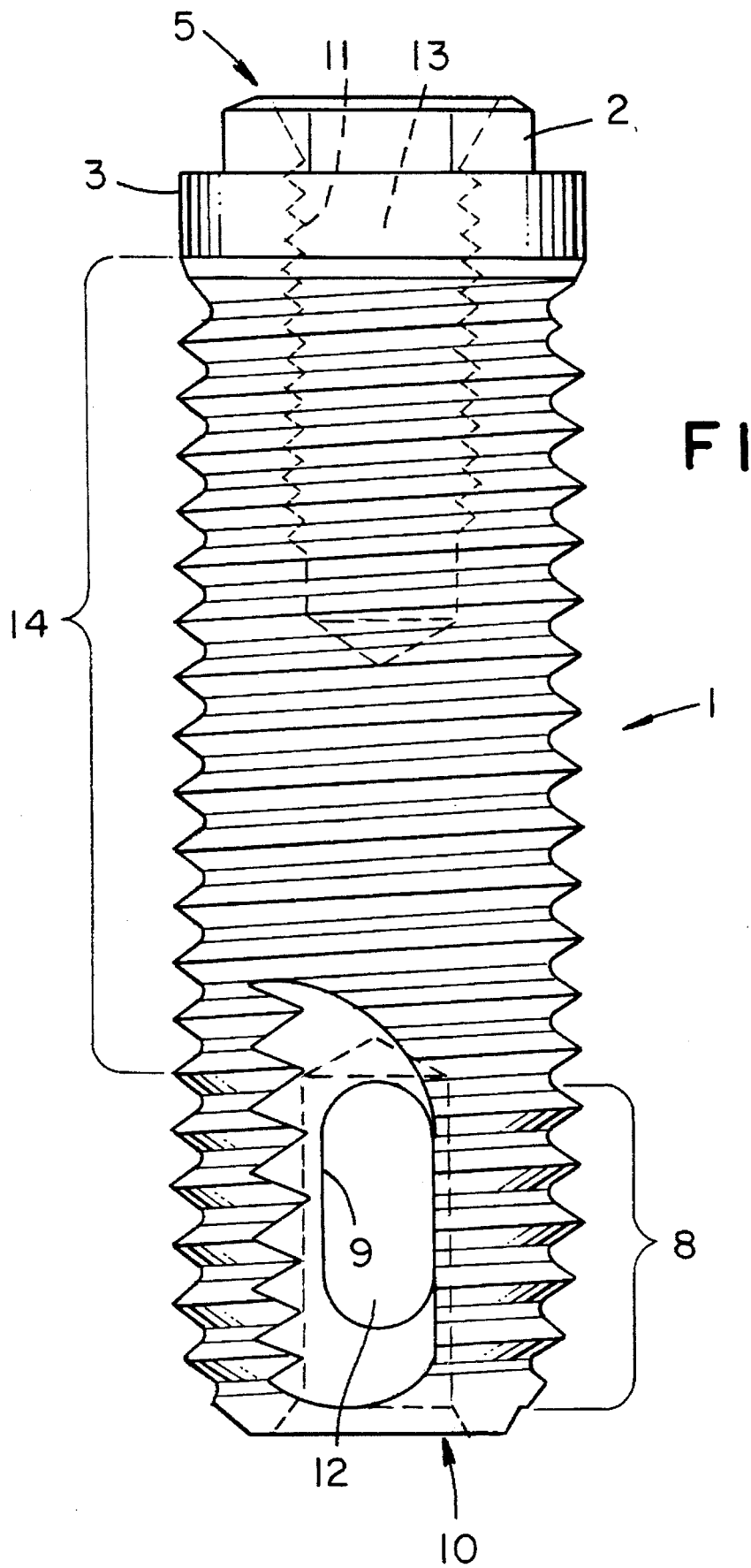
FIG. 1 is a self-tapping, generally cylindrical, endosseous dental implant having a roughened middle region on its external threaded surface, a smoother proximal end, and a smoother distal self-tapping threaded end.

FIG. 1 shows endosseous dental implant 1 having a generally cylindrical external shape. At distal end 10 of implant 1 are uncoated, self-tapping threads S, through-hole 9, and internal cavity 12 that receives bone chips and fluid formed as implant 1 is inserted into a generally cylindrical passage formed in the jawbone of a patient to receive implant 1. At proximal end 5 of implant 1 is uncoated, unthreaded, relatively smooth annular portion 3. Atop annular portion 3 is multi-sided, external wrench-engaging surface 2. Inside implant 1 and extending downwardly and inwardly from proximal end 5 is internal passage 13.

Internal passage 13 has an internally-threaded region 11 that can engage a complementary, threaded adapter. The darkened, external, threaded, middle region 14 is relatively rough, with the average peak-to-valley distance of the surface texture being 25 microns or greater which is at least 25% greater than the roughness of the uncoated self-tapping threads 8 at distal end or uncoated proximal end surfaces 2 and 3. HA coating, TPS coating, grit blasting can be used to form the relatively rough surface 14. Middle region 14 may also be coated with a high crystallinity HA material that has a surface roughness of less than 25 microns as measured from peak-to-valley of the surface texture. Instead of being roughened, middle region 14 can simply be coated, as with HA coating or TPS coating, in contrast to uncoated annular portion 3 and uncoated distal end 10. Middle region 14 could alternatively be unthreaded, and either roughened or coated.

Figure 2:
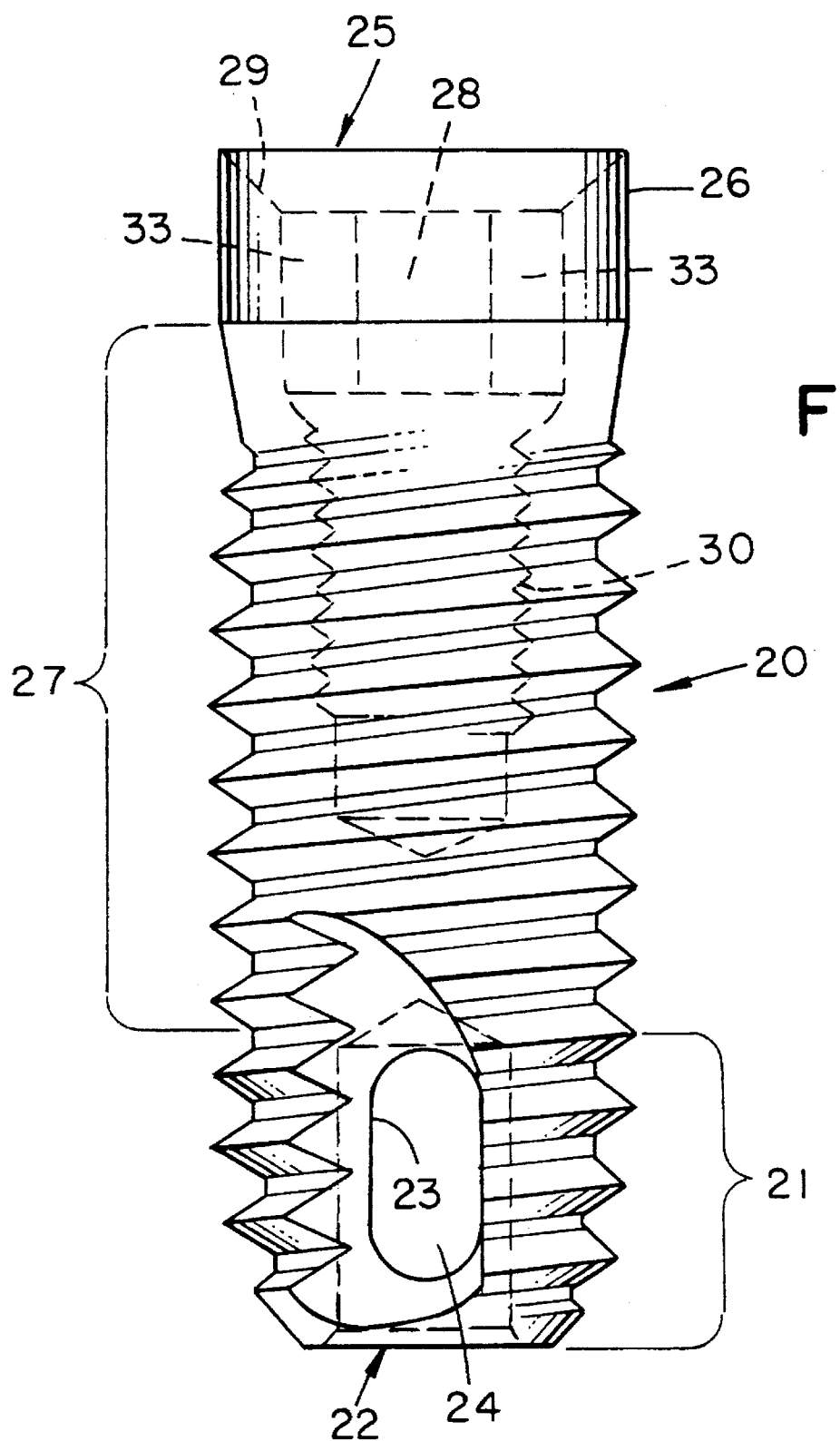
FIG. 2 is another self-tapping, generally cylindrical, endosseous dental implant having a roughened middle region on its external threaded surface, a smoother proximal end, and a smoother distal self-tapping threaded end.

FIG. 2 shows endosseous dental implant 20 having a generally cylindrical shape and including relatively smooth distal end 22 that includes self-tapping threads 21. Above distal end 22 is through-hole 23 and internal cavity 24 that receives blood, bone chips and other debris formed as implant 20 is screwed into a generally cylindrical passage formed in the jawbone of a person to receive implant 20. Implant 20 also includes, at its proximal end 25, relatively smooth annular surface 26 above roughened region 27.

Inside implant 20 is internal passage 28 that includes, just below proximal opening 25, an annular-shaped, chamfered region 29. Below chamfered region 29 is multi-sided, wrench-engaging surface 33, and, below surface 33, internal threaded passage 30. The internal threads in passage 30 are formed and shaped to engage a threaded adapter or abutment or, alternatively, a cementable adapter.

Implant 20 has a darkened, external, threaded, middle region 27 with a surface that is relatively rough, with the average peak-to-valley distance of the surface texture being 25 microns or greater which is at least 25% greater than the roughness of the uncoated self-tapping threads 21 at distal end and relatively smooth uncoated proximal end 26. HA coating, TPS coating, grit blasting can be used to form the relatively rough surface 27. Middle region 27 may also be coated with a high crystallinity HA material that has a surface roughness of less than 25 microns as measured from peak-to-valley of the surface texture. Instead of being roughened, middle region 27 can simply be coated, as with HA coating or TPS coating, in contrast to uncoated annular surface 26 and distal end 22. Middle region 27 could alternatively be unthreaded, and either roughened or coated.

A study entitled "Optimization Of Surface Micromorphology For Enhanced Osteoblast Responses In Vitro" by K. Bowers et al., published in the *Journal of Maxillofacial Implants,* 1992, Vol. 3, pp. 302–310, suggested that bone cell attachment to dental implant surfaces improves if the surface roughness of the implant that contacts bone tissue has randomized roughness. Preferred embodiments of the implants of this invention therefore include relatively rough, external middle regions with random roughness.

What is claimed is:

1. An endosseous dental implant having a generally cylindrical shape and including, at its distal end, self-tapping threads, and at its proximal end, wrench-engaging surfaces for engaging a tool to place said implant in a generally-cylindrical passage formed in the jawbone of a person to receive said implant, said distal end and said proximal end having a roughness of up to about 20 microns measured by the average difference between the peaks and valleys of the surface texturing, and, between said distal and proximal ends, a relatively rough, middle region having a roughness of at least about 25 microns, measured by the average difference between the peaks and valleys of the surface texturing.

2. The dental implant of claim 1 wherein said relatively rough, middle region of the external surface of the implant has randomized surface roughness.

3. The dental implant of claim 1 or claim 2 wherein the distal end of the implant includes at least one through-hole and at least one internal cavity of sufficient size and shape to receive and hold solids and liquids formed by the self-cutting threads as the implant is inserted into said passage.

4. The implant of claim 1 wherein said relatively rough, middle region is HA coated.

5. The implant of claim 1 wherein said relatively rough, middle region is coated with titanium plasma spray.

6. The implant of claim 1 wherein said relatively rough, middle region is formed by grit-blasting.

7. The endosseous dental implant of claim 1 or claim 2 or claim 4 or claim 5 or claim 6 wherein said wrench-engaging surfaces are at the proximal end of said implant and project upwardly from said top end.

8. The endosseous dental implant of claim 1 or claim 2 or claim 4 or claim 5 or claim 6 further comprising a top surface at said proximal end, and an external wall that includes said distal end, said proximal end, and said middle region, and wherein said wrench-engaging surfaces are inside said implant, below the top surface of said implant, and within the external wall of said implant.

9. An endosseous dental implant having a generally cylindrical shape including, at its distal end, self-tapping threads, and at its proximal end, wrench-engaging surfaces adapted to engage a tool to place said implant in a generally-cylindrical passage formed in the jawbone of a person to receive said implant, and, between said distal end and said proximal end, a relatively rough, externally-threaded middle region having a roughness at least about 25 percent greater than the roughness of said distal end and said proximal end, said roughness being measured by the average difference between the peaks and valleys of the surface texturing.

10. The dental implant of claim 9 wherein said relatively rough, middle region of the external surface of the implant has randomized surface roughness.

11. The dental implant of claim 9 or claim 10 wherein the distal end of the implant includes at least one through-hole and at least one internal cavity of sufficient size and shape to receive and hold solids and liquids formed by the self-cutting threads as the implant is inserted into said passage.

12. The implant of claim 9 wherein said relatively rough, middle region is HA coated.

13. The implant of claim 9 wherein said relatively rough, middle region is coated with titanium plasma spray.

14. The implant of claim 9 wherein said relatively rough, middle region is formed by grit-blasting.

15. The endosseous dental implant of claim 9 or claim 10 or claim 12 or claim 13 or claim 14 wherein said distal end and said proximal end have a roughness of up to about 20 microns measured by the average difference between the peaks and valleys of the surface texturing.

16. The endosseous dental implant of claim 9 or claim 10 or claim 12 or claim 13 or claim 14 wherein said wrench-engaging surfaces are at the proximal end of said implant and project upwardly from said proximal end.

17. An endosseous dental implant having a generally cylindrical shape and including, at its distal end, self-tapping threads, and at its proximal end, wrench-engaging surfaces for engaging a tool to place said implant in a generally-cylindrical passage formed in the jawbone of a person to receive said implant, said distal end and said proximal end being uncoated, and, between said distal and said proximal ends, a coated middle region.

18. The dental implant of claim 17 wherein said distal end of the implant includes at least one through-hole and at least one internal cavity of sufficient size and shape to receive and hold solids and liquids formed by the self-cutting threads as the implant is inserted into said passage.

19. The dental implant of claim 17 wherein said middle region is coated with Hydroxylapatite.

20. The dental implant of claim 17 wherein said middle region is coated with Titanium Plasma Spray.

21. The dental implant of claim 17 wherein said wrench-engaging surfaces are at the top end of said implant and project upwardly from said top end.

22. The dental implant of claim 17 further comprising a top surface at said proximal end and an external wall that includes said distal end, said proximal end, and said middle region, and wherein said wrench-engaging surfaces are inside said implant, below the top surface of said implant, and within the external wall of said implant.

23. The dental implant of claim 1 or claim 2 or claim 3 or claim 4 or claim 5 or claim 6 or claim 7 or claim 7 or claim 8 or claim 9 or claim 10 or claim 11 or claim 12 or claim 13 or claim 14 or claim 15 or claim 16 or claim 17 or claim 18 or claim 19 or claim 20 or claim 21 or claim 22 wherein said-middle region is externally-threaded.

24. The dental implant of claim 17 or claim 18 or claim 19 or claim 20 or claim 21 or claim 22 wherein the uncoated portion of said proximal end includes an annular neck region.

\* \* \* \* \*